United States Patent [19]
Brattsand et al.

[11] 3,983,233
[45] Sept. 28, 1976

[54] COMPOSITIONS AND METHOD OF TREATING WITH STEREOISOMERIC MIXTURES OF 2-UNSYMMETRICAL 16,17-METHYLENEDIOXY STEROIDS

[75] Inventors: Ralph Lennart Brattsand, Lund; Bo Thuresson af Ekenstam, Molndal; Karl Göran Claeson, Saro; Bror Arne Thalen, Lund, all of Sweden

[73] Assignee: AB Bofors, Bofors, Sweden

[22] Filed: Nov. 6, 1975

[21] Appl. No.: 629,389

Related U.S. Application Data

[63] Continuation-in-part of Ser. No. 360,051, May 14, 1973, Pat. No. 3,929,768.

[30] Foreign Application Priority Data

May 19, 1972 Sweden.............................. 6644/72

[52] U.S. Cl............................ 424/241; 260/397.45; 260/239.55 D
[51] Int. Cl.².......................................... C07J 17/00
[58] Field of Search............ 424/241; 260/239.55 D

[56] References Cited
UNITED STATES PATENTS

| | | | |
|---|---|---|---|
| 3,048,581 | 8/1962 | Fried............................ | 260/239.55 |
| 3,128,238 | 4/1964 | Mallett.............................. | 195/51 |
| 3,133,940 | 5/1964 | Oughton et al................ | 260/397.45 |

*Primary Examiner*—Elbert L. Roberts
*Attorney, Agent, or Firm*—Gordon W. Hueschen

[57] ABSTRACT

Novel steroids having the general formula:

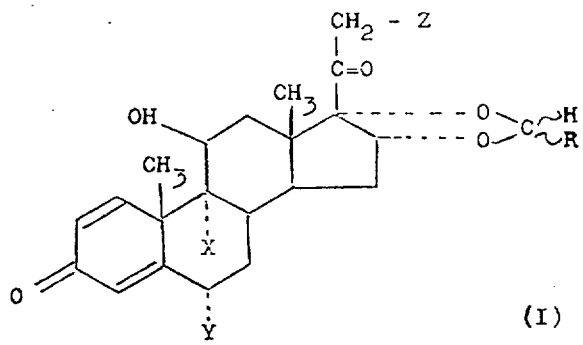

(I)

wherein X and Y are independently selected from hydrogen and fluorine, X being selected from hydrogen and fluorine when Y is hydrogen and X being fluorine when Y is fluorine, Z is selected from hydroxyl and esterified hydroxyl preferably containing a maximum of 12 carbon atoms, if any, in the esterifying group, R is selected from straight and branched hydrocarbon chains having 2–10 carbon atoms; processes for the preparation of said steroids; compositions containing said steroids; and method of treating inflammation therewith. The steroids are physiologically active compounds possessing anti-inflammatory activity. This application claims pharmaceutical compositions and method of treating employing the novel steroid steroisomeric mixtures.

48 Claims, No Drawings

COMPOSITIONS AND METHOD OF TREATING WITH STEREOISOMERIC MIXTURES OF 2-UNSYMMETRICAL 16,17-METHYLENEDIOXY STEROIDS

This application is a continuation-in-part of our prior-filed, co-pending application Ser. No. 360,051, filed May 14, 1973, now U.S. Pat. No. 3,929,768, issued Dec. 30, 1975. The subject matter presently claimed herein was subjected to a restriction requirement in the parent application under date of Oct. 11, 1973, which restriction requirement was made final on Nov. 16, 1973.

The present invention refers to new physiologically active steroids, to processes for their manufacture, to preparations containing such steroids, and to method of treating inflammation therewith. The new physiologically active steroids according to the invention have the general formula:

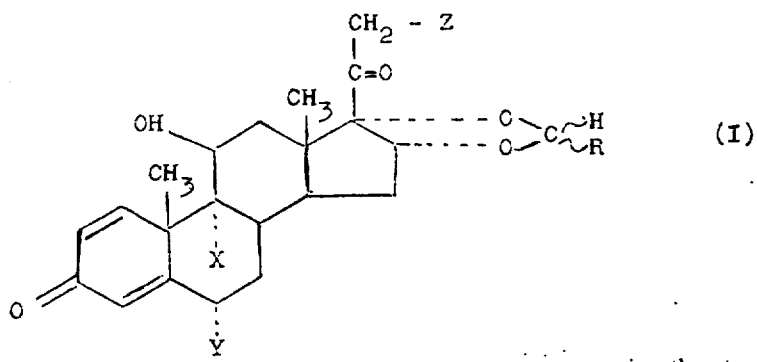

(I)

wherein X and Y are independently selected from hydrogen and fluorine, X being selected from hydrogen and fluorine when Y is hydrogen and X being fluorine when Y is fluorine, Z is selected from hydroxyl and esterified hydroxyl preferably containing a maximum of 12 carbon atoms, if any, in the esterifying group, R is selected from straight and branched hydrocarbon chains having 2–10 and preferably 2–6 carbon atoms.

The above-mentioned steroids may be prepared by reacting a steroid having the general formula:

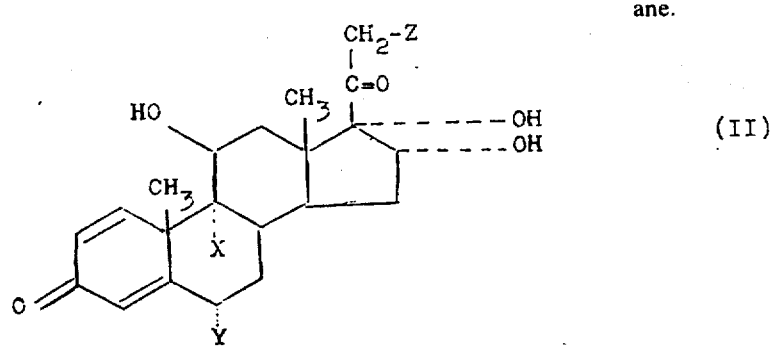

(II)

with an aldehyde having the general formula

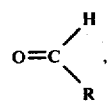

wherein R has the meaning given above, to the formation of desired steroid having formula (I) above, whereby if in the steroid obtained Z is hydroxyl, said hydroxyl is possibly esterified. The esterification may be carried out with a fatty acid with a straight or branched hydrocarbon chain having 1–12 carbon atoms, such fatty acid being for instance: acetic acid, propionic acid, butyric acid, valeric acid, isovaleric acid, trimethyl acetic acid, hexanoic acid, tert-butyl acetic acid, octanoic acid, or with a heterocyclic carboxylic acid, such as pyridine-3-, pyridine-4-, benzofuran-2-carboxylic acids or a menthoxymethyl carboxylic acid. To prepare water-soluble steroid derivatives the esterification is suitably carried out with dicarboxylic acids, preferably acids having 2–12 carbon atoms, or with phosphoric or sulphuric acids.

The reaction between the starting compound II and the carbonyl compound is suitably carried out by adding the steroid II to a solution of the carbonyl compound together with an acid catalyst for instance perchloric acid, p-toluene sulphonic acid, hydrochloric acid etc., in dioxane or equivalent solvent, the reaction mixture being then taken up in methylene chloride and neutralized and the acetal derivative formed being isolated and purified by gel filtration on a suitable material, for instance cross-linked dextrane gels of Sephadex LH-type or copolymers of vinyl acetate, such as Merckogel OR-PVA, in equilibrium with suitable solvents, for instance halogen hydrocarbons, ethers or esters, such as ethyl acetate, chloroform, methylene chloride, ethylene chloride, tetrahydrofurane and dioxane.

To prepare the particularly useful 21-acyloxy derivatives the free acid, its halogenide or anhydride may be used in the esterification.

For the preparation of the 21-phosphate derivatives phosphoroxy chloride in the presence of a tertiary base, for instance pyridine-3-ethylamine or the like, is used.

The intermediary chloride formed is hydrolyzed with water in the presence of the same tertiary base. If it is desired, the 21-phosphate may be converted to its alkali salt by means of an alkali metal hydroxide, such as sodium or potassium hydroxide, or an alkali metal carbonate, such as sodium or potassium carbonate.

All of the steroids of the instant disclosure may, if desired, be separated in their stereo isomers by gel filtration on a suitable material in conformity with U.S. Ser. No. 359,913, filed May 14, 1973, now U.S. Pat. No. 3,928,326.

The stereo isomery is due to the space orientation about the 2'-carbon atom of the dioxolane ring.

The invention will now be further illustrated by non-limiting examples. In the examples there is used for the chromatography a column having a length of 85 cm, an inner diameter of 2.5 cm, the flow rate being 1 ml/min. The molecular weights are determined by mass spectroscopy. The retention volumes given in the examples refer to the use of chloroform as an eluant. All the melting points are determined by means of a Reichert melting point microscope, and all derivatives melt under decomposition.

Example 1

16α, 17α-(20'-Hydrogen-2'-ethyl) methylene dioxy-9-fluoropregna-1,4-diene-11β,21-diol-3,20-dione.

To a solution of 59.0 mg newly distilled propion aldehyde and 0.1 ml 72 % perchloric acid in 30 ml thoroughly purified and dired dioxane 200.0 mg of triamcinolon were added in portions for 30 minutes. The reaction mixture was then allowed to stand for further 5.5 hours at room temperature under stirring and was then diluted with 200 ml methylene chloride. The solution was washed twice with a 15 % potassium bicarbonate solution and then three times with water and dried. The solvents were evaporated in vacuum, the residue was taken up in ether and precipitated with petroleum ether. The dried crude product (220.0 mg) was chromatographed on a column packed with hydroxy-propylated, cross-linked dextran gel (Sephadex LH 20, molecular weight range 100–4000; Pharmacia Fine Chemicals, Uppsala, Sweden) using chloroform as an eluant, the retention volume being 840–990 ml. This resulted in 174.6 mg (79 %) pure isomer mixture having the follwing characteristics: Melting point about 155°–97°C; $[\alpha]_D^{25} = +97.5°$ (c=0.2 in $CH_2Cl_2$); molecular weight = 434 (theor. 434.5).

Similar separation results were obtained by using a gel of copolymers of vinyl acetate (Merckogen OR-PVA 2000, molecular weight range up to 1000), as well as using, in addition to chloroform, methylene chloride, ethylene chloride, ethyl acetate, tetrahydrofurane and dioxane as eluants for both types of gel materials.

Examples 2–12

In a manner analogous to that described in Example 1 the substances given in Tables 1–3 below were prepared, purified and chromatographed.

Table 1

| Example No. | 16α, 17α-derivative of triameinolone with: | $[\alpha]_D^{25}$ (c=0.2 in $CH_2Cl_2$)° | Mp. °C | Molecular weight, found: | calculated: | Retention volume mls |
|---|---|---|---|---|---|---|
| 2 | n-butyraldehyde | + 94.0 | 130–45 | 448 | 448.5 | 822–984 |
| 3 | n-valeric aldehyde | + 86.4 | 96–108 | 462 | 462.6 | 780–924 |
| 4 | n-caproic aldehyde | + 82.3 | 94–100 | 476 | 476.6 | 702–828 |
| 5 | n-decylaldehyde | + 76.4 | 70–84 | 532 | 532.7 | 540–630 |

Table 2

| Example No. | 16α, 17α-derivative of fluocinolone with: | $[\alpha]_D^{25}$ (c=0.2 in $CH_2Cl_2$)° | Mp. °C | Molecular weight found: | calculated: | Retention volume mls |
|---|---|---|---|---|---|---|
| 6 | n-butyraldehyde | + 88.3 | 155–65 | 476 | 476.5 | 1130–1320 |
| 7 | n-caproic aldehyde | + 83.6 | 150–7 | 494 | 494.6 | 870–1000 |
| 8 | n-caprylic aldehyde | + 73.1[1] | 117–30 | 522 | 522.6 | 750–850 |

[1] c = 0.1 in $CH_2Cl_2$

Table 3

| Example No. | 16α, 17α-derivative of prednacinolone with | $[\alpha]_D^{25}$ (c=0.2 in $CH_2Cl_2$)° | Mp. °C | Molecular weight found: | calculated: | Retention volume mls |
|---|---|---|---|---|---|---|
| 9 | n-butyraldehyde | +96.9 | 215–22 | 430 | 430.5 | 456–540 |
| 10 | n-caproic aldehyde | +87.3 | 190–4 | 458 | 458.6 | 414–498 |
| 11 | n-caprylic aidehyde | +82.0 | 75–90 | 486 | 486.7 | 372–420 |
| 12 | n-decylaldehyde | +79.1 | 65–80 | 514 | 514.7 | 336–390 |

Examples 13

16α, 17α-(2'-hydrogen-2'-n-propyl)methylene dioxy-11β-hydroxy-21-(benzofurane-2-carbonyloxy)-9-fluorpregna-1,4-diene-3,20-dione.

A solution of 50.0 mg of 16α, 17α-(2'-Hydrogen-2'-n-propyl)methylenedioxy-9-fluorpregna-1,4-diene-11β,21-diol-3,20-dione in 2 ml dry pyridine was added to 56.4 mg benzofurane-2-carboxylic acid chloride dissolved in 1 ml of dry dioxane. The reaction mixture was allowed to stand under stirring at room temperature over night, the main part of the solvents were evaporated in vacuum and the residue was poured into 20 ml of 3 % ammonium chloride solution. The precipitate obtained was separated by centrifugation and dissolved in 75 ml of chloroform. The chloroform solution was washed once with 15 % sodium bicarbonate solution, three times with water, dried over magnesium sulphate and evaporated in vacuum. The residue was dissolved in ether and precipitated with petroleum ether. The dried, solid crude product (54.5 mg) was chromatographed on Sephadex LH-20 using chloroform as an eluant. The retention volume was 372–420 ml. This resulted in 48.5 mg (73 %) 21-benzofurane-2-carboxylic ester of a pure isomeric mixture of the desired compound having the following characteristics: Melting point about 175°–90°C; $[\alpha]_D^{25} = +150.2°$ (c=0.2 in $CH_2Cl_2$); molecular weight = 592 (theor. 592.7).

EXAMPLES 14–36.

In a manner analogous to that described in Example 13 the 21-esters of the compounds prepared in Examples 1–12 and shown in Table 4 below were prepared, purified and chromatographed.

The acid chlorides used for the esterification are abbreviated in Table 4 in the following manner:

NAC = nicotinic acid chloride
IAC = isonicotinic acid chloride
AAC = acetyl chloride
VAC = valeric acid chloride
BAC = benzofurane-2-carboxylic acid chloride.

times with water. The water phase was neutralized with 1.4 ml of 5 % sodium carbonate solution to pH 7.0 and freeze-dried. The solid substance (95.3 mg) was taken up in dry methanol and the insoluble part was separated by centrifugation. The methanol solution was treated with excess of Dowex 50W-X8 (H-form), (this material is a cation exchange resin consisting of a copolymer of styrene and divinyl benzene (8 %) and sold by Dow Chemical Company, USA), filtrated and transferred to a column packed with Sephadex LH-20 (length 80 cm, inner diameter 25 mm) and eluated (flow rate 1 ml/min.) with methanol of weak sulphuric acid acidity (Retention volume 255–330 ml). The methanol was evaporated in vacuum, the residue was taken up in water, neutralized to pH 7.0 with 5 % sodium carbonate solution and freeze-dried.

The resulting solid substrate was slurried in dry methanol. The methanol solution was centrifugated and evaporated to 1 ml and petroleum ether was then added. This resulted in 22.7 mg (45 %) of 21-disodiumphosphate of 16α,17α(2'-hydrogen-2'-n-propyl)-methylenedioxy-9-fluorpregna-1,4-diene-11β,21-diol-3,20-dione with $R_f = 0.78$ (thin layer chromatography on cellulose with isopropanol:ammonia:water 7:1:2).

Elementary analysis: Calculated for $C_{25}H_{32}O_9FPNa_2$ (572.488); C, 52.45; H, 5.63; P, 5.41. Obtained: C, 51.87; H, 5.41; P, 5.59.

Table 4

| Example No. | the 21-ester of the compound of Ex. No. | with | $[\alpha]_D^{25}$ (c=0.2 in $CH_2Cl_2$)° | Mp. °C | Molecular weight, found: | calculated: | Retention volume, mls |
|---|---|---|---|---|---|---|---|
| 14 | 2 | NAC | +119.4 | 212–35 | 553 | 553.6 | 342–420 |
| 15 | 2 | IAC | +115.5 | 198–201 | 553 | 553.6 | 320–380 |
| 16 | 2 | AAC | +83.3 | 216–34 | 490 | 490.6 | 310–360 |
| 17 | 2 | VAC | +88.2 | 224–43 | 532 | 532.7 | 270–315 |
| 18 | 4 | VAC | +79.3 | 189–97 | 560 | 560.7 | 235–80 |
| 19 | 5 | VAC | +71.8 | 162–63 | 616 | 616.8 | 234–58 |
| 20 | 6 | BAC | +138.9 | 197–200 | 610 | 610.7 | 282–348 |
| 21 | 6 | NAC | +108.3 | 187–99 | 571 | 571.6 | 282–348 |
| 22 | 6 | AAC | +78.8 | 260–78 | 508 | 508.6 | 335–395 |
| 23 | 6 | VAC | +81.2 | 238–45 | 550 | 550.7 | 270–306 |
| 24 | 7 | AAC | +73.0 | 250–55 | 536 | 536.6 | 336–84 |
| 25 | 8 | VAC | +69.2 | 192–98 | 606 | 606.8 | 245–75 |
| 26 | 9 | BAC | +142.9 | 120–30 | 574 | 574.7 | 230–270 |
| 27 | 9 | NAC | +120.6 | 110–25 | 535 | 535.6 | 275–340 |
| 28 | 9 | AAC | +86.2 | 157–63 | 472 | 472.6 | 240–65 |
| 29 | 9 | VAC | +93.9 | 166–78 | 514 | 514.7 | 220–50 |
| 30 | 10 | VAC | +83.3 | 177–87 | 542 | 542.7 | 222–46 |
| 31 | 11 | BAC | +112.2 | 103–12 | 658 | 658.8 | 204–28 |
| 32 | 11 | AAC | +78.4 | 185–7 | 528 | 528.7 | 225–50 |
| 33 | 11 | VAC | +77.4 | 153–4 | 570 | 570.8 | 216–46 |
| 34 | 12 | BAC | +123.5 | 79–90 | 658 | 658.8 | 198–222 |
| 35 | 12 | AAC | +75.2 | 142–5 | 556 | 556.7 | 215–35 |
| 36 | 12 | VAC | +96.7 | 108–10 | 598 | 598.8 | 195–225 |

EXAMPLE 37

The 21-disodium phosphate of 16α, 17α-(2'-hydrogen-2'-n-propyl)methylenedioxy-9-fluorpregna-1,4-diene-11β,21-diol-3,20-dione.

To a solution of 0.016 ml newly distilled phosphoroxychloride in 2.0 ml of dry pyridine a solution of 40.0 mg of 16α,17α-(2'-hydrogen-2'-n-propyl)methylenedioxy-9-fluorpregna-1,4-diene-11β,21-diol-3,20-dione (II) in 2.0 ml of dry pyridine was added under stirring at −26°C. The temperature was allowed to rise to −10°C, whereafter the reaction mixture was allowed to stand a few minutes in the cold. Water (0.16 ml) was added drop-wise, the temperature not being allowed to exceed −10°C. After 13 minutes the pyridine was evaporized in vacuum, the residue was taken up in chloroform and the chloroform solution was extracted three

EXAMPLE 38

The 21-disodium phosphate of 16α,17α-(2'-hydrogen-2'-n-propyl)methylene dioxy-6α,9-difluorpregna-1,4-diene-11β,21-dion-3,20-dione was obtained in a manner analogous to that described in Example 37 and showed the following data:

Retention volume: 250 – 305 ml
Rf = 0.69 (thin layer chromatography on cellulose with isopropanol:ammonia:water 7:1:2).

Elementary analysis: Calculated for $C_{25}H_{31}O_9F_2PNa_2$ (590,473): C, 50.85; H, 5.29; P, 5.25. Obtained: C, 50.53; H, 5.12; P, 5.38.

Below there are given examples of galenic preparations prepared in a conventional manner:

| Example 39. | Ointment, fat, anhydrous. | |
|---|---|---|
| Steroid | | 0.001 – 0.2 |
| Cetanol | | 5 |
| Liquid paraffin | | 20 |
| Vaseline | to | 100 g |

| Example 40. | Cream. | |
|---|---|---|
| Steroid | | 0.001 – 0.2 |
| Monolein | | 2.5 |
| Wool fat | | 5 |
| Vaseline | | 42 |
| Citric acid | | 0.3 |
| Sodium citrate | | 0.9 |
| Water | to | 100. g |

| Example 41. | Liniment. | |
|---|---|---|
| Steroid | | 0.001 – 0.2 |
| Cetanol | | 3.2 |
| Stearol | | 0.2 |
| Polyoxyethylene sorbitane monolaurate | | 2 |
| Sorbitane monopalmitate | | 0.5 |
| Propylene glycol | | 4.8 |
| Metagin[a] | | 0.08 |
| Propagin | | 0.02 |
| Water | to | 100. g |

[a] methylester of parahydroxybenzoic acid

| Example 42. | Tincture. | |
|---|---|---|
| Steroid | | 3–500 mg |
| Ethanol 60 % | to | 100 ml |

| Example 43. | Suspension for injection. | | |
|---|---|---|---|
| Steroid | 0.05 | – | 10 mg |
| Sodium carboxymethyl cellulose | 7 | | mg |
| Sodium chloride | 7 | | mg |
| Tween 80[a] | 0.5 | | mg |
| Phenyl carbinol | 8 | | mg |
| Water, sterile | to | 1 | ml |

[a] Polyoxyethylene(20)sorbitane monooleate.

| Example 44. | Foam aerosol. | |
|---|---|---|
| Steroid | | 0.001 – 0.2 |
| Glycerol | | 4 |
| N-cetylstearyl alcohol | | 0.2 |
| Cetylstearyl alcohol | | 3 |
| Isopropylmyristate | | 2 |
| Metagin | | 0.1 |
| Water | | 80 |
| Tetrafluordichloroethane/ difluordichloromethane 40:60 | to | 100. g |

All steroids of the instant invention are physiologically active compounds, possessing antiinflammatory activity. The antiinflammatory activity of the substances according to the invention was investigated in granulom test on rats subjected to adrenalectomy. The experimental procedure used corresponds largely to that described by G. Engelhardt: Arzneimittel-Forschung, 13, p. 588, 1963. According to this procedure the test substances are applied topically in the implanted cotton wads. It is thereby possible to study the local antiinflammatory effect in granuloma and also systemic effects in the form of retrogression of thymus and inhibition of bodyweight growth.

Yound male rats of the Sprague-Dawley strain weighing about 110–130 g were subjected to adrenalectomy under ether narcosis. Two sterilized cotton wads of each about 6 mg were implanted simultaneously subcutaneously on the lateral side of the spinal. After awakening the animals were stored 5 per cage and were supplied with normal food and 1 % sodium chloride solution as drinking water. On the eighth test day the animals were sacrificed by ether narcosis. The granulomas formed around the cotton wads were carefully recovered and thymus and body weights were measured. The two granulomas from each animal were dried over night at 80°C and weighed. After subtraction of the initial weight of the cotton wads the weight increase was used as a measure of the granulom growth.

The test substances were used dissolved in ethyl acetate. Under aseptic conditions 0.05 ml of said solutions were injected into each of the cotton wads, whereafter the solvent was allowed to evaporate in desiccator. Normally 3 concentrations of each test substance with the standard doses 3.3, 30 and 270 γ/animal were investigated. Each test group normally comprised 10 rats. The cotton wads of the control group were injected with only ethyl acetate, but were in other respects treated in the same way. When considering the effects of the test substances the average values of granulom growth, thymus weight and body weight increase day 0–8 were measured in each group in absolute figures and in % of the corresponding figure of the control group. Dose-response curves were drafted and used for estimating the doses giving 50% reduction of granulom growth and of thymus weight and 25% decrease of body weight increase.

The results of testing the steroids according to the invention as per the procedure described above are summarized in table 5 below. From said table it is clear that the investigated compounds of the invention are physiologically active substances showing significantly stronger antiinflammatory effect than steroids of the prior art. The dose required for obtaining 50% reduction of the granulom growth is lower for the compounds of the present invention than the corresponding dose of the reference substances triamcinolone acetonide, fluocinolone acetonide and prednacinolone acetonide, which substances have wide-spread use.

Moreover it is clear from the experimental data presented that the new compounds possess a better relation between the local antiinflammatory activity (inhibition of granulom growth) and systemic effects in the form of weight decrease of thymus and in the form of decreased body growth. With regard to the reference substances higher doses are required for obtaining 50% reduction of granulom growth than for negatively affecting thymus and body weights. Contrary to this, for the new compounds of this invention a 50% antiinflammatory activity was obtained at lower doses than the doses resulting in the systemic effects in question. Therefore, the new compounds of the invention show surprisingly a better relation between desirable main effect and non-desirable side effects.

The compounds may be used to treat inflammation in any living mammalian animal body by administering thereto an effective antiinflammatory amount of the compound in any suitable form and by any suitable mode of administration, e.g. topically, orally, or parenterally, in the same manner and in the same areas of treatment as their parent compounds, but generally with greater efficiency and therefore generally in lower dosages and according to somewhat lower dosage regimens.

As representative of living animal bodies which may be treated with the compounds and compositions of the invention, and according to the method of treating of the invention, for alleviation of the same and/or similar conditions as those described, the following may be mentioned inter alia: domestic animals such as dogs and cats, farm animals such as horses, cows, sheep and goats.

Table 5

Table summarizing biological effects of investigated compounds.

| Compound according to Ex. No. | Required dose γ/animal to obtain: | | |
|---|---|---|---|
| | 50 % inhibition of | | 25 % inhibition of |
| | Granuloma growth | Thymus weight | Body weight increase |
| Triamcinolone acetonide | 125 | 70 | 100 |
| 1 | 35 | 100 | 140 |
| 2 | 10 | >30 | >30 |
| 3 | <3 | 70 | 170 |
| 4 | 17 | 130 | >270 |
| 5 | <30 | >30 | >30 |
| Fluocinolone acetonide | 50 | 14 | 20 |
| 6 | 5 | 10 | 50 |
| 7 | <3 | 25 | 30 |
| 8 | <30 | >30 | >30 |
| Prednacinolone acetonide | 270 | 105 | >270 |
| 9 | 100 | 80 | 80 |
| 10 | 10 | 175 | 90 |
| 11 | <30 | >270 | 30 |
| 12 | <30 | >270 | 270 |
| 13 | <3 | 25 | 20 |
| 14 | 7 | 35 | 10 |
| 15 | 15 | 17 | 25 |
| 16 | <3 | 30 | 20 |
| 17 | <7 | 50 | 30 |
| 20 | <3 | 10 | 10 |
| 21 | 10 | 30 | 20 |
| 22 | <3 | 10 | 5 |
| 26 | <3 | 60 | 40 |
| 27 | 3 | 90 | 70 |
| 29 | <3 | 60 | 20 |

Particularly preferred compounds are:

physiologically-active steroids of the present invention. Such preparations containing the new corticoids of the present invention are intended to be used in local treatment of various inflammatory conditions, where it is well-known that corticoids are effective. Examples of such conditions are most kinds of exzemas and other dermatoses, psoriasis, bronchial asthma, as well as other obstructive lung diseases. (L. Goodman and A. Gilman: The pharmacological basis of therapeutics, Fourth Ed., The MacMillan Co., London 1970; A. Biedermann Wien, Med. Wochenschr. 121 (1971) 331). Within these areas there is a clinical demand not so much for getting new corticoids with a higher antiinflammatory potency but for compounds with a lower extent of unfavorable systemic side effects. Therefore, the relation between the local and the systemic effects of the new corticoids of the present invention have been investigated in the cotton pellet test and found to be more favorable than for the parent compounds triamcinolone acetonide, fluocinolone acetonide and prednacinolone acetonide, as already set forth in the foregoing.

Depending on where the inflammation is located, different modes of local administration are possible, such as percutaneous, inhalation, parenteral, and rectal, as shown by the following compositions. One important aim of the formulation design is a high bioavailability of the active steroid ingredient. In the case of percutaneous formulations, this can be advantageously attained when the steroid is dissolved, with a high thermodynamic activity, in a suitable hydrophilic solution system mainly consisting of a plurality of different pharmaceutically acceptable glycols, e.g., propylene glycol and butandiol-1,3, either alone or in combination with water. The formulation can be in the form of an ointment, a cream, a paste, a liniment, a lotion, a solution or a gel, consisting of a one-phase or two-phase system. In the later case the solution-system with the steroid can make up the disperse as well as the continuous phase. In such a two-phase system there is also present a lipophilic phase consisting of conventional ointment ingredients, such as petrolatum, mineral oil, isopropyl myristate, different waxes, cetanol, steryl alcohol, stearic acid and monoglycerides. Furthermore, the formulation can comprise an emulsifying

| | |
|---|---|
| Ex. 2 | 16α,17α-(2'-hydrogen-2'-n-propyl)methylenedioxy-9-fluorpregna-1,4-diene-11β,21-diol-3,20-dione. |
| Ex. 3 | 16α,17α-(2'-hydrogen-2'-n-butyl)methylenedioxy-9-fluorpregna-1,4-diene-11β,21-diol-3,20-dione. |
| Ex. 6 | 16α,17α-(2'-hydrogen-2'-n-propyl)methylenedioxy-6α,9-difluorpregna-1,4-diene-11β,21-diol-3,20-dione. |
| Ex. 7 | 16α,17α-(2'-hydrogen-2'-n-pentyl)methylenedioxy-6α,9-difluorpregna-1,4-diene-11β,21-diol-3,20-dione. |
| Ex. 10 | 16α,17α-(2'-hydrogen-2'-n-pentyl)methylenedioxy-pregna-1,4-diene-11β,21-diol-3,20-dione. |
| Ex. 14 | 16α,17α-(2'-hydrogen-2'-n-propyl)methylenedioxy-11β-hydroxy-21-nicotinoyloxy-9-fluorpregna-1,4-diene-3,20-dione. |
| Ex. 16 | 16α,17α-(2'-hydrogen-2'-n-propyl)methylenedioxy-11β-hydroxy-21-acetoxy-9-fluorpregna-1,4-diene-3,20-dione. |
| Ex. 20 | 16α,17α-(2'-hydrogen-2'-n-propyl)methylenedioxy-11β-hydroxy-21-(benzofurane-2-carbonyloxy)-6α,9-difluorpregna-1,4-diene-3,20-dione. |
| Ex. 22 | 16α,17α-(2'-hydrogen-2'-n-propyl)methylenedioxy-11β-hydroxy-21-acetoxy-6α,9-difluorpregna-1,4-diene-3,20-dione. |
| Ex. 26 | 16α,17α-(2'-hydrogen-2'-n-propyl)methylenedioxy-11β-hydroxy-21-(benzofurane-2-carbonyloxy)pregna-1,4-diene-3,20-dione. |
| Ex. 29 | 16α,17α-(2'-hydrogen-2'-n-propyl)methylenedioxy-11β-hydroxy-21-valeroyloxypregna-1,4-diene-3,20-dione. |

The present application also relates to pharmaceutical formulations or compositions containing the new agent with a suitable HLB* value and in some cases also a preservative.

*HLB= Hydrophile-Lipophile Balance

The following further examples are representative of preparations intended for different modes of local administration. The amount of steroid in the percutaneous formulations is usually 0.001–0.2% by weight, preferably 0.005–0.05% by weight.

| Composition 1 Ointment | | |
|---|---|---|
| 16α,17α-(2'-hydrogen-2'-n-propyl)methylenedioxypregna-1,4-diene-11β,21-diol-3,20-dione | 0.025 | g |
| Propylene glycol | 9.0 | g |
| White wax | 5.0 | g |
| Mineral Oil | 16.0 | g |
| White petrolatum | 70.0 | g |

| Composition 2 Cream | | | |
|---|---|---|---|
| 16α,17α-(2'-hydrogen-2'-n-propyl)methylenedioxypregna-1,4-diene-11β,21-diol-3,20-dione | | 0.025 | g |
| Propylene glycol | | q.s.*) | |
| Cetomacrogol | | 2.0 | g |
| Cetosteryl alcohol | | 7.0 | g |
| Mineral oil | | 6.0 | g |
| White petrolatum | | 15.0 | g |
| Chlorcresol | | 0.1 | g |
| Water | to | 100.0 | g |

*)amount necessary to dissolve the steroid

| Composition 3 Liniment | | | |
|---|---|---|---|
| 16α,17α-(2'-hydrogen-2'-n-propyl)methylenedioxypregna-1,4-diene-11β,21-diol-3,20-dione | | 0.025 | g |
| Propylene glycol | | q.s.*) | |
| Cetanol | | 3.2 | g |
| Steryl alcohol | | 0.2 | g |
| Polyoxyethylene Sorbitan Monolaurate | | 2.0 | g |
| Sorbitan Monopalmitate | | 0.5 | g |
| Methyl hydroxybenzoate | | 0.08 | g |
| Propyl hydroxybenzoate | | 0.02 | g |
| water | to | 100.0 | g |

*)amount necessary to dissolve the steroid

| Composition 4 Gel | | |
|---|---|---|
| 16α,17α-(2'-hydrogen-2'-n-propyl)methylenedioxypregna-1,4-diene-11β,21-diol-3,20-dione | 0.025 | g |
| Propylene Glycol | 35.0 | g |
| Carbopol 934(TM)*) | 1.0 | g |
| Triethanolamine | 1.0 | g |
| Methyl hydroxybenzoate | 0.08 | g |
| Propyl hydroxybenzoate | 0.02 | g |
| Water to | 100.0 | g |

*)Carboxyvinyl polymer

| Composition 5 Solution | | | |
|---|---|---|---|
| 16α,17α-(2'-hydrogen-2'-n-propyl)methylenedioxypregna-1,4-diene-11β,21-dinol-3,20-dione | | 0.025 | g |
| Isopropanol | | 40.0 | g |
| Water | to | 100.0 | g |

| Composition 6 Foam Aerosol | | |
|---|---|---|
| 16α,17α-(2'-hydrogen-2'-n-propyl)methylenedioxypregna-1,4-diene-11β,21-diol-3,20-dione | 0.025 | g |
| Glycerol | q.s.*) | |
| Propylene glycol | q.s.*) | |
| Cetylstearyl alcohol | 0.2 | g |
| Isopropyl myristate | 2.0 | g |
| Methyl hydroxybenzoate | 0.1 | g |
| Water | 80.0 | g |
| -Tetrafluorodichloroethane/Difluorodichloromethane 40:60 to | 100.0 | g |

*)amount necessary to dissolve the steroid

| Composition 7 Percutaneous Spray | | |
|---|---|---|
| 16α,17α-(2'-hydrogen-2'-n-propyl)methylenedioxypregna-1,4-diene-11β,21-diol-3,20-dione | 0.025 | g |
| Isopropanol | 80.0 | g |
| Isopropyl myristate | 10.0 | g |
| Trichlorofluoromethane/Dichlorodifluoromethane 50:50 to | 100.0 | g |

| Composition 8 Suspension for Injection | | | |
|---|---|---|---|
| 16α,17α-(2'-hydrogen-2'-n-propyl)methylene-dioxypregna-1,4-diene-11β,21-diol-3,20-dione | | 0.05 – 10 | mg |
| Sodium carboxy methyl cellulose | | 7.0 | mg |
| Sodium chloride | | 7.0 | mg |
| Polyoxyethylene(20)sorbitan monooleate | | 0.5 | mg |
| Phenyl carbinol | | 8.0 | mg |
| Water, sterile | to | 1. | ml |

COMPOSITION 9

Pressurized Aerosol for Inhalation

Pressurized aerosols containing steroids are intended for oral or nasal inhalation. The aerosol system is arranged so that each measured dose contains 10–1000μg, preferably 20–250μg, of the steroid. More active steroids are administered at the lower part of this range.

The micronized steroid contains particles basically less than 5μm, which are suspended in the propellent mixture by the aid of a surfactant such as sorbitan trioleate, oleic acid, lecithin, or sodium dioctylsulfosuccinate.

| | |
|---|---|
| 16α,17α-(2'-hydrogen-2'-n-propyl)methylene-dioxypregna-1,4-diene-11β,21-diol-3,20-dione micronized | 0.1 % w/w |
| Sorbitan trioleate | 0.7 % w/w |
| Trichloromonofluoromethane | 24.8 % w/w |
| Dichlorotetrafluoroethane | 24.8 % w/w |
| Dichlorodifluoromethane | 49.6 % w/w |

COMPOSITION 10

Powder Aerosol for Inhalation

The micronized steroid contains particles basically less than 5μm, which are mixed with a carrier substance such as, for example, lactose. The mixture is dispensed in single unit doses and the powder mixture is inhaled from a suitable powder inhaler. Each single dose contains 10–1000μg, preferably 20–250 μg of the steroid. More active steroids are administered at the lower part of this range.

| | |
|---|---|
| 16α,17α-(2'-hydrogen-2'-n-propyl)methylene-dioxypregna-1,4-diene-11β,21-diol-3,20-dione micronized | 0.1 mg |
| Lactose | 50.0 mg |

The new physiologically active steroids can of course also be given orally, e.g., in a single dose of 0.1–10 mg, preferably 0.5–2.5 mg, especially in a daily dose of 0.5–20 mg.

| Composition 11 Tablets | | |
|---|---|---|
| Each tablet contains: | | |
| Steroid | 0.1 – 10 | mg |
| Maize Starch | 25.0 | mg |
| Lactose | 190.0 | mg |
| Gelatin | 1.5 | mg |
| Talc | 12.0 | mg |
| Magnesium stearate | 1.5 | mg |

For some types of inflamation, it can be of advantage to combine the steroid with other active substances such as local analgetics and antibiotics, as illustrated by the following compositions.

| Composition 12 Rectal Ointment | | |
|---|---|---|
| 16α,17α-(2'-hydrogen-2'-n-propyl)methylene-dioxypregna-1,4-diene-11β,21-diol-3,20-dione | | 0.5 mg |
| Lidocaine | | 25.0 mg |
| Mineral Oil | | 0.2 g |
| White petrolatum | to | 1.0 g |

| Composition 13 Suppository | |
|---|---|
| 16α,17α-(2'-hydrogen-2'-n-propyl)methylene-dioxypregna-1,4-diene-11β,21-diol-3,20-dione | 1 mg |
| Lidocaine | 60 mg |
| Massa supp Imhausen | q.s. |

| Composition 14 Ointment with Steroid + Antibioticum | |
|---|---|
| 16α,17α-(2'-hydrogen-2'-n-propyl)methylene-dioxypregna-1,4-diene-11β,21-diol-3,20-dine | 0.025 g |
| Neomycin sulfate | 0.5 g |
| Propylene glycol | 9.0 g |
| White wax | 5.0 g |
| Mineral oil | 16.0 g |
| White petrolatum | 70.0 g |

The antiinflammatory properties of the dermal preparations of the new compounds according to the present invention have been evaluated in the vasoconstriction test in human volunteers. This test was chosen inasmuch as a close correlation between the activity in this test model and actual clinical efficacy has been reported (McKenzie Archs. Derm 86 (1962) 611). The vasoconstriction test was performed according to Christie and Moore: Brit. J. Derm. (1970) 82 suppl. 6.93. To delineate the area of application on the forearm, double adhesive Blenderm tape, in which 32 holes 8 mm φ had been punched, was used. Three mg of the steroid formulation was in each case randomly applicated in the holes and the whole area was covered with a plastic film. Six hours later the tape was removed and the intensity of vasoconstriction was estimated 7, 8, 10, 12, 14, 24, 28, 32 and 48 hours after application. The quantification of the degree of vasoconstriction was

| Score | Degree of vasoconstriction |
|---|---|
| 0 | Normal skin |
| 1 | Slight vasoconstriction |
| 2 | Vasoconstriction |

| Score | Degree of vasoconstriction |
|---|---|
| 3 | Intense vasoconstriction |

The grading of the vasoconstriction was performed according to double-blind technique. Each ointment was applied on ten test sites. With this technique, the activity of formulations of 16 α, 17α-(2'-hydrogen-2'-n-propyl)methylenedioxypregna-1,4-diene-11β, 21-diol-3,20-dione was compared with Synalar ointment, containing 0.025% fluocinolone acetonide, as a reference. The compositions of the formulations were as follows:

| 16α,17α-(2'-hydrogen-2'-n-propyl)methylene-dioxypregna-1,4-diene-11β,21-diol-3,20-dione | | Propylene glycol | Mineral oil | White petrolatum | White wax |
|---|---|---|---|---|---|
| | | % by weight | | | |
| 1 | 25 mg | 9 | 16 | 70 | 5 |
| 2 | 10 mg | 4 | 21 | 70 | 5 |
| 3 | 5 mg | 2 | 23 | 70 | 5 |
| 4 | 2.5 mg | 1 | 24 | 70 | 5 |

According to the results of this test, the formulations of 16α, 17α-(2'-hydrogen-2'-n-propyl)methylenedioxypregna-1,4-diene-11β, 21-diol-3,20-dione induced the same vasoconstriction as Synalar ointment 0.025% even at a concentration which was 5 to 10 times lower.

the preferred compounds of the compositions and method of treating according to the present invention are the 16α, 17α derivatives of fluocinolone, triamcinolone, prednacinolone, all having a 2'-hydrogen and a 2'-n-propyl group, that is, 16α, 17α-(2'-hydrogen-2'-n-propyl)methylenedioxy-9-fluorpregna-1,4-diene-11β, 21-diol-3,20-dione; 16α,17α-(2'-hydrogen-2'-n-propyl)-methylenedioxy-6α,9-fluorpregna-1,4-diene-11β,21-diol-3,20-dione; and 16α, 17α-(2'-hydrogen-2'-n-propyl)methylenedioxypregna-1,4-diene-11β,21-diol-3,20-dione, and the 21-acetates thereof.

Various modifications in the compounds, compositions, and methods of the invention will be apparent to one skilled in the art and may be made without departing from the spirit or scope thereof, and it is therefore to be understood that the invention is to be limited only by the scope of the appended claims.

We claim:

1. A pharmaceutically-active composition, suitable for use in the treatment of inflammation, containing as active ingredient an effective antiinflammatory amount of a steroid compound, in combination with a pharmaceutically-acceptable carrier, said steroid compound being a stereoisomeric mixture of a 2'-unsymmetrical 16,17-methylenedioxy steroid having the general formula

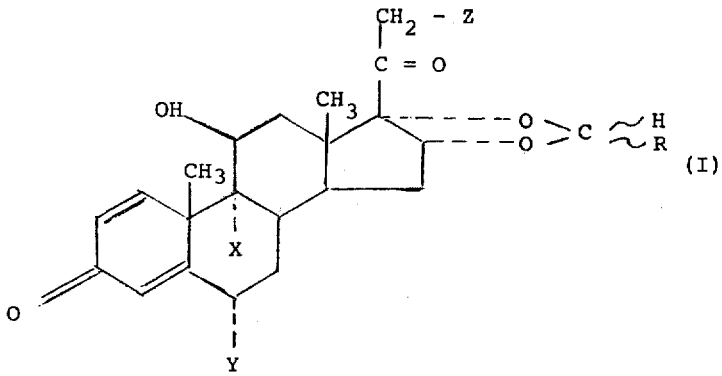

wherein X and Y are independently selected from hydrogen and fluorine, X being selected from hydrogen and fluorine when Y is hydrogen and X being fluorine when Y is fluorine, Z is selected from hydroxyl and esterified hydroxyl wherein the hydroxyl group is esterified with a member of the group consisting of phosphoric and sulphuric acids, dicarboxylic acids having 2 to 12 carbon atoms, inclusive, pyridine-3-carboxylic acid, pyridine-4-carboxylic acid, benzofurane-2-carboxylic acid, and menthoxymethylcarboxylic acid, and lower-alkanoic acids having up to a maximum of 8 carbon atoms, and R is selected from straight and branched hydrocarbon chains having 2 to 10 carbon aoms, inclusive.

2. The composition of claim 1, wherein R in the active ingredient is selected from straight and branched hydrocarbon chains having 2 to 6 carbon atoms, inclusive.

3. The composition of claim 1, wherein X in the active ingredient is fluorine and Z is hydroxyl.

4. The composition of claim 1, wherein Y in the active ingredient is fluorine.

5. The composition of claim 1, wherein Z in the active ingredient is hydroxyl esterified with an acid selected from acetic acid, propionic acid, butyric acid, valeric acid, isovaleric acid, trimethylacetic acid, hexanoic acid, tert.-butyl acetic acid, and octanoic acid.

6. The composition of claim 1, wherein Z in the active ingredient is hydroxyl esterified with an acid selected from pyridine-3-, pyridine-4-, benzofurane-2-carboxylic acid, and menthoxymethylcarboxylic acid.

7. The composition of claim 1, wherein Z in the active ingredient is hydroxyl esterified with an acid selected from dicarboxylic acids having 2 to 12 carbon atoms, inclusive.

8. The composition of claim 1, wherein Z in the active ingredient is hydroxyl esterified with an acid selected from phosphoric and sulphuric acids.

9. The composition of claim 1, wherein the active ingredient is selected from the group consisting of 16α,17α-(2'-hydrogen-2'-n-propyl)methylenedioxy-9-fluorpregna-1,4-diene-11β,21-diol-3,20-dione; 16α,17α-(2'-hydrogen-2'-n-butyl)methylenedioxy-9-fluorpregna-1,4-diene-11β,21-diol-3,20-dione; 16α,17α-(2'-hydrogen-2'-n-propyl)methylenedioxy-6α,9- difluorpregna-1,4-diene-11β,21-diol-3,20-dione; 16α,17α-(2'-hydrogen-2'-n-pentyl)methylenedioxy-6α,9-difluorpregna-1,4-diene-11β,21-diol-3,20-dione; 16α,17α-(2'-hydrogen-2'-n-pentyl)methylenedioxy-pregna-1,4-diene-11β,21-diol-3,20-dione; 16α,17α-(2'-hydrogen-2'-ethyl)methylenedioxy-9-fluorpregna-1,4-diene-11β,21-diol-3,20-dione; 16α,17α-(2'-hydrogen-2'-n-pentyl)methylenedioxy-9-fluorpregna-1,4-diene-11β,21-diol-3,20-dione; 16α,17α-(2'-hydrogen-2'-n-heptyl)methylenedioxy-pregna-1,4-diene-11β,21-diol-3,20-dione; 16α,17α-(2'-hydrogen-2'-n-nonyl)-methylenedioxy-pregna-1,4-diene-11β,21-diol-3,20-dione; 16α,17α-(2'-hydrogen-2'n-heptyl)methylenedioxy-6α,9-difluorpregna-1,4-diene-11β,21-diol-3,20-dione; and 16α,17α-(2'-hydrogen-2'-n-propyl)methylene-dioxypregna-1,4-diene-11β,21-diol-3,20-dione.

10. The composition of claim 1, wherein the active ingredient is selected from the group consisting of 16α,17α-(2'-hydrogen-2'-n-propyl)methylenedioxy-11β-hydroxy-21-nicotinoyloxy-9-fluorpregna-1,4-diene-3,20-dione; 16α,17α-(2'-hydrogen-2'-n-propyl)-methylenedioxy-11β-hydroxy-21-acetoxy-9-fluorpregna-1,4-diene-3,20-dione; 16α,17α-(2'-hydrogen-2'-n-propyl)methylenedioxy-11β-hydroxy-21-(benzofurane-2-carbonyloxy)-6α,9-difluorpregna-1,4-diene-3,20-dione; 16α,17α-(2'-hydrogen-2'-n-propyl)methylenedioxy-11β-hydroxy-21-acetoxy-6α,9-difluorpregna-1,4-diene-3,20-dione; 16α,17α-(2'-hydrogen-2'-n-propyl)methylenedioxy-11β-hydroxy-21-(benzofurane-2-carbonyloxy)pregna-1,4-diene-3,20-dione; 16α,17α-(2'-hydrogen-2'-n-propyl)methylenedioxy-11β-hydroxy-21-valeroyloxypregna-1,4-diene-3,20-dione; 16α,17α-(2'-hydrogen-2'-n-propyl)methylenedioxy-11β-hydroxy-21-(benzofurane-2-carbonyloxy)-9-fluorpregna-1,4-diene-3,20-dione; 16α,17α-(2'-hydrogen-2'-n-propyl)methylenedioxy-11β-hydroxy-21-isonicotinoyloxy-9-fluorpregna-1,4-diene-3,20-dione; 16α,17α-(2'-hydrogen-2'-n-propyl)methylenedioxy-11β-hydroxy-21-valeroyloxy-9-fluorpregna-1,4-diene-3,20-dione; 16α,17α-(2'-hydrogen-2'-n-propyl)-methylenedioxy-11β-hydroxy-21-nicotinoyloxy-6α,9-difluorpregna-1,4-diene-3,20-dione; 16α,17α-(2'-hydrogen-2'-n-propyl)methylenedioxy-11β-hydroxy-21-nicotinoyloxypregna-1,4-diene-3,20-dione; and 16α,17α-(2'-hydrogen-2'-n-propyl)methylenedioxy-11β-hydroxy-21-acetoxypregna-1,4-diene-3,20-dione.

11. The composition of claim 1, in the form of an ointment.

12. The composition of claim 1, wherein the active steroid ingredient is dissolved in a hydrophilic solution system.

13. The composition of claim 12, wherein the system comprises a plurality of different pharmaceutically-acceptable glycols.

14. The composition of claim 1, wherein the composition is a percutaneous formulation for local administration, wherein the amount of active steroid ingredient is between 0.001 and 0.2 percent by weight.

15. The composition of claim 1, wherein the composition is a percutaneous formulation for local administration, wherein the amount of active steroid ingredient is between 0.005 and 0.05 percent by weight.

16. The composition of claim 1, wherein the composition is in a form suitable for inhalation administration.

17. The composition of claim 1, wherein the active steroid ingredient is selected from the group consisting of 16α,17α-(2'-hydrogen-2'-n-propyl)methylenedioxy-9-fluorpregna-1,4-diene-11β,21-diol-3,20-dione; 16α,17α-(2'-hydrogen-2'-n-propyl)methylenedioxy-6α,9-difluorpregna-1,4-diene-11β,21-diol-3,20-dione; and 16α,17α-(2'-hydrogen-2'-n-propyl)methylenedioxypregna-1,4-diene-11β,21-diol-3,20-dione.

18. A method of treating inflammation in a mammalian body in need of such treatment comprising the step of administering thereto an effective antiinflammatory amount of a stereoisomeric mixture of a 2'-unsymmetrical 16,17-methylenedioxy steroid having the general formula I as defined in claim 1.

19. The method of claim 18, wherein the active antiinflammatory steroid is administered in the form of a pharmaceutically active composition in combination with a pharmaceutically acceptable carrier therefor.

20. The method of claim 18, wherein R in the said steroid is selected from straight and branched hydrocarbon chains having two to six carbon atoms, inclusive.

21. The method of claim 18, wherein X in the said steroid is fluorine and Z is hydroxyl.

22. The method of claim 18, wherein Y in the said steroid is fluorine.

23. The method of claim 18, wherein Z in the said steroid is hydroxyl esterified with an acid selected from acetic acid, propionic acid, butyric acid, valeric acid, isovaleric acid, trimethylacetic acid, hexanoic acid, tert.-butyl acetic acid, and octanoic acid.

24. The method of claim 18, wherein Z in the said steroid is hydroxyl esterified with an acid selected from pyridine-3-, pyridine-4-, benzofurane-2-carboxylic acid, and menthoxymethylcarboxylic acid.

25. The method of claim 18, wherein Z in the said steroid is hydroxyl esterified with an acid selected from dicarboxylic acids having 2 to 12 carbon atoms, inclusive.

26. The method of claim 18, wherein Z in the said steroid is hydroxyl esterified with an acid selected from phosphoric and sulfuric acids.

27. The method of claim 18, wherein the said steroid is selected from the group consisting of 16α,17α-(2'-hydrogen-2'-n-propyl)methylenedioxy-9-fluorpregna-1,4-diene-11β,21-diol-3,20-dione; 16α,17α-(2'-hydrogen-2'-n-butyl)methylenedioxy-9-fluorpregna-1,4-diene-11β,21-diol-3,20-dione; 16α,17α-(2'-hydrogen-2'-n-propyl)methylenedioxy-6α,9-difluorpregna-1,4-diene-11β,21-diol-3,20-dione; 16α,17α-(2'-hydrogen-2'-n-pentyl)methylenedioxy-6α,9-difluorpregna-1,4-diene-11β,21-diol-3,20-dione; 16α,17α-(2'-hydrogen-2'-n-pentyl)methylenedioxy-pregna-1,4-diene-11β,21-diol-3,20-dione; 16α,17α-(2'-hydrogen-2'-ethyl)-methylenedioxy-9-fluorpregna-1,4-diene-11β,21-diol-3,20-dione; 16α,17α-(2'-hydrogen-2'-n-pentyl)methylenedioxy-9-fluorpregna-1,4-diene-11β,21-diol-3,20-dione; 16α,17α-(2'-hydrogen-2'-n-heptyl)methylenedioxy-pregna-1,4-diene-11β,21-diol-3,20-dione; 16α,17α-(2'-hydrogen-2'-n-nonyl)methylenedioxy-pregna-1,4-diene-11β,21-diol-3,20-dione; 16α,17α-(2'-hydrogen-2'n-heptyl)methylenedioxy-6α,9-difluoropregna-1,4-diene-11β,21-diol-3,20-dione; and 16α,17α-(2'-hydrogen-2'n-propyl)methylene-dioxypregna-1,4-diene-11β,21-diol-3,20-dione.

28. The method of claim 18, wherein the said steroid is selected from the group consisting of 16α,17α-(2'-hydrogen-2'-n-propyl)methylenedioxy-11β-hydroxy-21-nicotinoyloxy-9-fluorpregna-1,4-diene-3,20-dione; 16α,17α-(2'-hydrogen- 2'-n-propyl)methylenedioxy-11β-hydroxy-21-acetoxy-9-fluorpregna-1,4-diene-3,20-dione; 16α,17α-(2'-hydrogen-2'-n-propyl)methylenedioxy-11β-hydroxy-21-(benzofurane-2-carbonyloxy)-6α,9-difluorpregna-1,4-diene-3,20-dione; 16α,17α-(2'-hydrogen-2'-n-propyl)methylenedioxy-11β-hydroxy-21-acetoxy-6α,9-difluorpregna-1,4-diene-3,20-dione; 16α,17α-(2'-hydrogen-2'-n-propyl)methylenedioxy-11β-hydroxy-21-(benzofurane-2-carbonyloxy)pregna-1,4-diene-3,20-dione; 16α,17α-(2'-hydrogen-2'-n-propyl)methylenedioxy-11β-hydroxy-21-valeroyloxypregna-1,4-diene-3,20-dione; 16α,17α-(2'-hydrogen-2'-n-propyl)methylenedioxy-11β-hydroxy-21-(benzofurane-2-carbonyloxy)-9-fluorpregna-1,4-diene-3,20-dione; 16α,17α-(2'-hydrogen-2'-n-propyl)methylenedioxy-11β-hydroxy-21-isonicotinoyloxy-9-fluorpregna-1,4-diene-3,20-dione; 16α,17α-(2'-hydrogen-2'-n-propyl)methylenedioxy-11β-hydroxy-21-valeroyloxy-9-fluorpregna-1,4-diene-3,20-dione; 16α,17α-(2'-hydrogen-2'-n-propyl)methylenedioxy-11β-hydroxy-21-nicotinoyloxy-6α,9-difluorpregna-1,4-diene-3,20-dione; 16α,17α-(2'-hydrogen-2'-n-propyl)methylenedioxy-11β-hydroxy-21-nicotinoyloxypregna-1,4-diene-3,20-dione; and 16α,17α-(2'-hydrogen-2'-n-propyl)methylenedioxy-11β-hydroxy-21-acetoxypregna-1,4-diene-3,20-dione.

29. The method of claim 18, wherein the active anti-inflammatory steroid is administered in the form of an ointment.

30. The method of claim 18, wherein the active anti-inflammatory steroid is administered dissolved in a hydrophilic solution system.

31. The method of claim 30, wherein the system comprises a plurality of different pharmaceutically-acceptable glycols.

32. The method of claim 18, wherein the active anti-inflammatory steroid is administered in the form of a percutaneous pharmaceutically-active composition in combination with a pharmaceutically-acceptable carrier therefor wherein the amount of active steroid ingredient is between 0.001 and 0.2 percent by weight.

33. The method of claim 18, wherein the active anti-inflammatory steroid is administered in the form of a pharmaceutically-active composition in combination with a pharmaceutically-acceptable carrier therefor, wherein the composition is a percutaneous formulation for local administration, and wherein the amount of active steroid ingredient in said composition is between 0.005 and 0.05 percent by weight.

34. The method of claim 18, wherein the active anti-inflammatory steroid is administered by inhalation.

35. The method of claim 18, wherein the active anti-inflammatory steroid is 16α,17α-(2'-hydrogen-2'-n-propyl)methylenedioxy-9-fluorpregna-1,4-diene-11β,21-diol-3,20-dione; 16α,17α-(2'-hydrogen-2'-n-propyl)methylenedioxy-6α,9-difluorpregna-1,4-diene-11β,21-diol-3,20-dione; or 16α,17α-(2'-hydrogen-2'-n-propyl)methylenedioxypregna-1,4-diene-11β,21-diol-3,20-dione.

36. The composition of claim 1, wherein the composition is an aerosol formulation for oral or nasal administration and wherein the amount of active steroid ingredient in said formulation is adapted to provide between about 10 and 1,000 μg per unit dose.

37. The composition of claim 1, wherein the composition is an aerosol formulation for oral or nasal administration and wherein the amount of active steroid ingredient in said formulation is adapted to provide between about 20 and 250 μg per unit dose.

38. The method of claim 18, wherein the active anti-inflammatory steroid is administered in the form of an aerosol composition for oral or nasal inhalation and wherein said active steroid is administered in an amount between about 10 and 1,000 μg per unit dose.

39. The method of claim 18, wherein the active anti-inflammatory steroid is administered in the form of an aerosol composition for oral or nasal inhalation and wherein said active steroid is administered in an amount between about 20 and 250 μg per unit dose.

40. The composition of claim 1, wherein the composition is an oral unit dosage form containing between about 0.1 and 10 milligrams per unit dose of the active steroid ingredient.

41. The composition of claim 1, wherein the composition is an oral unit dosage form containing between about 0.5 and 2.5 milligrams per unit dose of the active steroid ingredient.

42. The method of claim 18, wherein the active anti-inflammatory steroid is administered orally in a unit dosage form containing between about 0.1 and 10 milligrams of said active anti-inflammatory steroid per unit dose.

43. The method of claim 18, wherein the active anti-inflammatory steroid is administered orally in a unit dosage form containing between about 0.5 and 2.5 milligrams of said active anti-inflammatory steroid per unit dose.

44. The method of claim 18, wherein the active anti-inflammatory steroid is administered in an oral dosage form in an amount between about 0.5 and 20 milligrams per daily dose.

45. The method of claim 44, wherein the active anti-inflammatory steroid is 16α,17α-(2'-hydrogen-2'-n-propyl)methylenedioxy-9-fluorpregna-1,4-diene-11β,21-diol-3,20-dione; 16α,17α-(2'-hydrogen-2'-n-propyl)methylenedioxy-6α,9-difluorpregna-1,4-diene-11β,21-diol-3,20-dione; or 16α,17α-(2'-hydrogen-2'-n-propyl)methylenedioxypregna-1,4-diene-11β,21-diol-3,20-dione.

46. The method of claim 32, wherein the active anti-inflammatory steroid is 16α,17α-(2'-hydrogen-2'-n-propyl)methylenedioxy-9-fluorpregna-1,4-diene-11β,21-diol-3,20-dione; 16α,17α-(2'-hydrogen-2'-n-propyl)methylenedioxy-6α,9-difluorpregna-1,4-diene-11β,21-diol-3,20-dione; or 16α,17α-(2'-hydrogen-2'-n-propyl)methylenedioxypregna-1,4-diene-11β,21-diol-3,20-dione.

47. The method of claim 38, wherein the active anti-inflammatory steroid is 16α,17α-(2'-hydrogen-2'-n-propyl)methylenedioxy-9-fluorpregna-1,4-diene-11β,21-diol-3,20-dione; 16α,17α-(2'-hydrogen-2'-n-propyl)methylenedioxy-6α,9-difluorpregna-1,4-diene-11β,21-diol-3,20-dione; or 16α,17α-(2'-hydrogen-2'-n-propyl)methylenedioxypregna-1,4-diene-11β,21-diol-3,20-dione.

48. The composition of claim 1, wherein X in the active ingredient is hydrogen, Y is hydrogen, and Z is selected from hydroxyl and esterified hydroxyl wherein the hydroxyl-group is esterified with a member of the group consisting of phosphoric and sulphuric acid, dicarboxylic acids having 2 to 12 carbon atoms, inclusive, pyridine-3-carboxylic acid, pyridine-4-carboxylic acid, benzofurane-2-carboxylic acid, and menthoxymethylcarboxylic acid, and lower-alkanoic acids having up to a maximum of 8 carbon atoms, and R is selected from straight and branched hydrocarbon chains having 2 to 10 carbon atoms, inclusive.

* * * * *